(12) United States Patent
Takamatsu

(10) Patent No.: US 10,532,112 B2
(45) Date of Patent: Jan. 14, 2020

(54) NON-HUMAN PRIMATE MODEL OF AGE-RELATED MACULAR DEGENERATION AND METHOD FOR PRODUCING SAME

(71) Applicants: Hamamatsu Pharma Research, Inc., Hamamatsu-shi (JP); Hideaki Hara, Gifu-shi (JP); Masamitsu Shimazawa, Gifu-shi (JP)

(72) Inventor: Hiroyuki Takamatsu, Hamamatsu (JP)

(73) Assignees: Hamamatsu Pharma Research, Inc., Hamamatsu-shi (JP); Hideaki Hara, Gifu-Shi (JP); Masamitsu Shimazawa, Gifu-Shi (JP)

( * ) Notice: Subject to any disclaimer, the term of this patent is extended or adjusted under 35 U.S.C. 154(b) by 0 days.

(21) Appl. No.: 15/853,190

(22) Filed: Dec. 22, 2017

(65) Prior Publication Data
US 2018/0272009 A1 Sep. 27, 2018

(30) Foreign Application Priority Data

Mar. 23, 2017 (JP) .................................. 2017-057515
Dec. 18, 2017 (JP) .................................. 2017-242163

(51) Int. Cl.
*A61K 48/00* (2006.01)
*A61K 49/00* (2006.01)
*A01K 67/027* (2006.01)

(52) U.S. Cl.
CPC ........ *A61K 49/0008* (2013.01); *A01K 67/027* (2013.01); *A01K 2207/20* (2013.01); *A01K 2227/106* (2013.01); *A01K 2267/035* (2013.01)

(58) Field of Classification Search
CPC ........................ A61K 49/008; A61K 2267/035
See application file for complete search history.

(56) References Cited

PUBLICATIONS

Pennesi et al. Mol Aspects Med. 33(4):487-509, 2012; see printout having pp. 1-40 (Year: 2012).*
Liu et al (2016) Investigative Ophthalmology and Visual Science 57(12):80 (Year: 2016).*
Okuno et al., *JNIOSH-SRR-No. 44*, 2014, pp. 67-70.
Ishida et al., "Characterization of a NalO3-induced retinal pigment epithelium degeneration rodent model for iPSC-RPE cell transplantation", *Kawasaki Medical Journal*, 2016, pp. 85-93, 42(2).
Cho et al., "Monocular retinal degeneration induced by intravitreal injection of sodium iodate in rabbit eyes", *Japanese Journal of Ophthalmology*, Feb. 23, 2016, pp. 226-237, vol. 60.

* cited by examiner

*Primary Examiner* — Marcia S Noble
(74) *Attorney, Agent, or Firm* — Leason Ellis LLP

(57) ABSTRACT

An object of the present invention is to provide a method for producing a non-human primate model of AMD, a method for evaluating the efficacy of a test substance in the prevention or treatment of AMD using the AMD animal model produced according to this method, and a method for screening substances effective in the prevention or treatment of AMD using the aforementioned AMD animal model. The method for preparing the AMD animal model consists of administering sodium iodate into a vitreous body of a non-human primate, and the method for evaluating the efficacy of a test substance in the prevention or treatment of AMD consists of preparing a non-human primate model of AMD according to the aforementioned method for preparing an AMD animal model, and evaluating the efficacy of the test substance in the prevention or treatment of AMD using the resulting AMD animal model.

7 Claims, 4 Drawing Sheets

Day 66

FLUORESCEIN ANGIOGRAPHY FINDINGS

NON-HUMAN PRIMATE MODEL OF AGE-RELATED MACULAR DEGENERATION AND METHOD FOR PRODUCING SAME

The present application claims priority on the basis of Japanese Patent Application No. 2017-57515, filed on Mar. 23, 2017, and Japanese Patent Application No. 2017-242163, filed on Dec. 18, 2017, the contents of which are incorporated herein by reference in their entirety.

FIELD OF THE INVENTION

The present invention relates to a method for producing a non-human primate model of age-related macular degeneration (AMD), a method for evaluating the efficacy of a test substance in the prevention or treatment of AMD using an AMD animal model produced according to this method, and a method for screening substances effective in the prevention or treatment of AMD using the aforementioned AMD animal model.

BACKGROUND OF THE INVENTION

AMD is one of the causes of blindness, and is associated with degeneration to retinal photoreceptor cells of the macula corresponding to the center of the ocular fundus. AMD is primarily classified into an atrophic form (dry type) and exudative form (wet type). In the atrophic form, photoreceptor cells along with retinal pigment epithelial cells and choroidal capillaries adjacent thereto gradually undergo degenerative atrophy. In the exudative form, choroidal vascularization occurs resulting in comparatively rapid progression of the disease due to hemorrhage and edema. In human atrophic AMD, degeneration (thinning and reduction) of retinal pigment epithelium (RPE) and thinning and loss of the outer nuclear layer (ONL) are observed in the retina.

A light-induced retinopathy model is known as an animal model that mimics atrophic AMD (see, for example, Non-Patent Document 1). In this model, intense light is used to induce retinopathy. In actuality, degeneration of the retina has been confirmed to occur in a mouse model of light-induced retinopathy. In addition, there are some AMD-like animal models in rodents and rabbits in which RPE have been caused to degenerate by systemic or intravitreal administration of sodium iodate (see, for example, Non-Patent Document 2 or 3).

In general, in the development of drugs for treatment of a disease, animal models of the disease are needed to investigate the therapeutic effects of a test substance. In order to obtain a proper evaluation of pharmacological efficacy using an animal model, it is imperative that the animal model used accurately reflect the pathology of the target disease. Since non-human primates are genetically, neuroanatomically and pharmacokinetically closer to humans than rodents, they can be expected to allow the obtaining of actions and effects that more closely approximate the actions and effects observed during administration to humans. Consequently, in order to develop a therapeutic drug that is effective in humans, it is preferable to use non-human primates as an animal model instead of rodents. Since the macula in particular is only present in primates, animal models of AMD using rodents or rabbits do not reflect the pathology of human AMD. Therefore, in order to develop preventive and therapeutic drugs for AMD, a non-human primate model of AMD is required that more accurately reflects the pathology of AMD.

PRIOR ART DOCUMENTS

Non-Patent Documents

[Non-Patent Document 1] Okuno, T., et al., Special Report of the National Institute of Occupational Safety and Health, 2014, Vol. 44, p. 67-70

[Non-Patent Document 2] Ishida, J., et al., Kawasaki Medical Journal, 2016, Vol. 42, No. 2, p. 85-93

[Non-Patent Document 3] Cho, et al., Japanese Journal of Ophthalmology, 2016, Vol. 60, p. 226-237

Problems to be Solved by the Invention

An object of the present invention is to provide a method for producing a non-human primate model of AMD, a non-human primate model of AMD, a method for evaluating the efficacy of a test substance in the prevention or treatment of AMD using an AMD animal model produced according to this method, and a method for screening substances effective in the prevention or treatment of AMD using the aforementioned AMD animal model.

SUMMARY OF THE INVENTION

Means for Solving the Problems

As a result of conducting extensive studies to solve the aforementioned problems, the inventor of the present invention found that, by administering sodium iodate directly into the vitreous body of a non-human primate, thinning of the ONL of and degeneration of RPE of the retina similar to that observed in age-related macular degeneration in humans can be induced in the periphery of the central fossa of the macula, which is responsible for the majority of visual function, while inhibiting the systemic effects of sodium iodate, thereby leading to completion of the present invention.

Namely, the method for producing an AMD animal model according to the present invention, a non-human primate model of AMD, a method for evaluating the efficacy of a test substance in the prevention or treatment of AMD using an AMD animal model produced according to this method, and a method for screening substances effective in the prevention or treatment of AMD using the aforementioned AMD animal model are as described in [1] to [11] below.

[1] A method for producing an animal model of AMD, including administering sodium iodate into a vitreous body of a non-human primate.

[2] The method for producing an animal model of AMD of [1] above, wherein the dosage of sodium iodate per vitreous body is 0.5 mg to 2.5 mg.

[3] The method for producing an animal model of AMD of [1] or [2] above, wherein a sodium iodate solution, obtained by dissolving sodium iodate in water or phosphate-buffered saline, is administered into a vitreous body.

[4] The method for producing an animal model of AMD of any of [1] to [3] above, wherein the animal is a cynomolgus monkey or rhesus monkey.

[5] The method for producing an animal model of AMD of any of [1] to [4] above, wherein thinning of the ONL and degeneration of RPE of the retina is observed in the periphery of the central fossa of the macula in the resulting animal model of AMD.

[6] The method for producing an animal model of AMD of any of [1] to [4] above, wherein geographic atrophy occurs in the ocular fundus of the resulting animal model of AMD.

[7] The method for producing an animal model of AMD of any of [1] to [6] above, wherein the resulting animal model of AMD is an animal model of atrophic AMD.

[8] A non-human primate model of AMD having thinning of the ONL and degeneration of RPE of the retina in the periphery of the central fossa of the macula.

[9] A non-human primate model of AMD, in which geographic atrophy is occurring in the ocular fundus.

[10] A method for evaluating the efficacy of a test substance in the prevention or treatment of AMD, including:

producing a non-human primate model of AMD according to the method for producing an animal model of AMD of any of [1] to [7] above, and evaluating the efficacy of a test substance in the prevention or treatment of AMD using the resulting animal model of AMD.

[11] A method for screening substances effective in the prevention or treatment of AMD, including:

producing a non-human primate model of AMD according to the method for producing an animal model of AMD of any of [1] to [7] above, evaluating the efficacy of a test substance in the prevention or treatment of AMD using the resulting animal model of AMD, and selecting the test substance as a substance effective in the prevention or treatment of AMD in the case one or more conditions selected from the group consisting of thinning of the ONL and degeneration of RPE of the retina are improved following ingestion of the test substance as compared with before ingesting the test substance.

Effects of the Invention

According to the method for producing an animal model of AMD of the present invention, a non-primate animal model can be produced that presents with the characteristic pathology of human AMD consisting of thinning of the ONL and degeneration of RPE of the retina.

The use of an animal model of AMD produced according to this method makes it possible to more accurately evaluate the efficacy of a test substance in the prevention or treatment of AMD as well as screen for substances that are effective in the prevention or treatment of AMD.

DETAILED DESCRIPTION OF THE INVENTION

Figure 1:
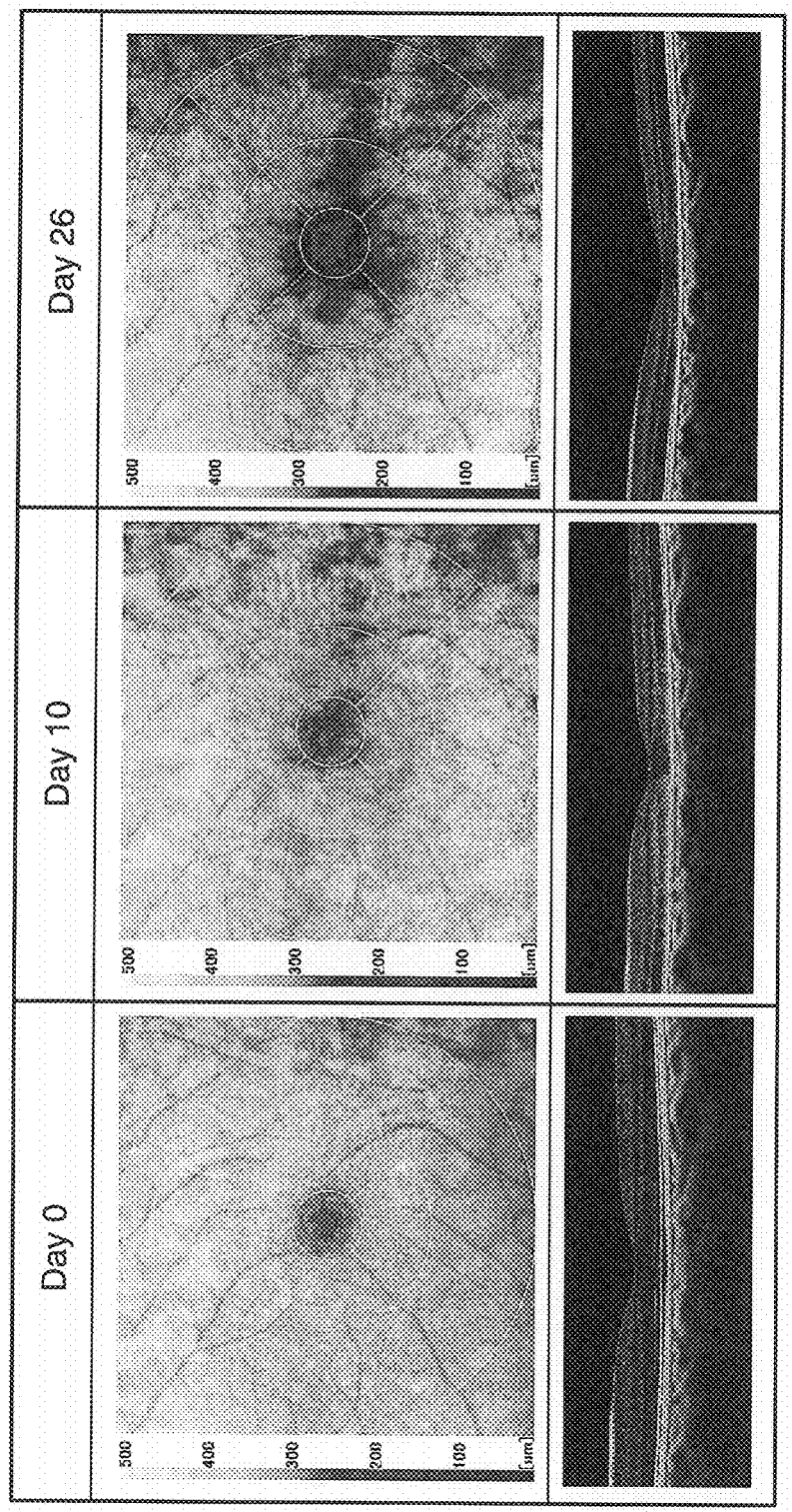
FIG. 1 depicts OCT images of the retina of an animal model intravitreally administered sodium iodate prior to administration of a sodium iodate solution (administration day 0), on day 10 after administration and on day 26 after administration in an Example 1.

The method for producing an animal model of AMD according to the present invention consists of administering sodium iodate into a vitreous body of a non-human primate. As a result of administering sodium iodate directly into a vitreous body, retinal degeneration, or in other words, thinning of the ONL, degeneration of RPE and geographic atrophy of the retina, similar to human AMD, and particularly human atrophic AMD, can be induced while inhibiting the systemic effects of sodium iodate.

Furthermore, the macular degeneration in the animal model of AMD produced according to the method for producing an animal model of AMD according to the present invention is similar to that observed in human AMD patients, and can be observed by combining various examinations commonly used to investigate the status of the retina, such as optical coherence tomography (OCT), funduscopy, fundus autofluorescence, fluorescein angiography or indocyanine green angiography. More specifically, the ONL thinning and RPE degeneration of the retina exhibited by an animal model of AMD produced according to the method for producing an animal model of AMD according to the present invention can be observed in the same manner as that observed in human AMD patients. For example, the ONL, macula and RPE of the eye can be observed directly by optical coherence tomography (OCT). Thinning of the ONL, disruption of the external limiting membrane, enhancement of choroidal signal and disappearance of the ellipsoid zone, interdigitation zone and outer nuclear layer are observed in OCT images of the eyes of the animal model of AMD according to the present invention in the same manner as observed in cases of atrophic AMD in humans. In addition, geographic atrophy of the ocular fundus of the AMD animal model is observed by funduscopy in the manner as observed in cases of atrophic AMD in humans. Atrophic sites present in geographic atrophy exhibit hypofluorescence in fundus autofluorescence and intense hyperfluorescence in fluorescein angiographic findings.

In the present invention, the amount of sodium iodate administered into a vitreous body is only required to be an amount sufficient for inducting retinal degeneration, and can be suitably determined in consideration of such factors as the species and age of non-human primate targeted for administration. In the case that the dosage of sodium iodate is excessively high, damage to the retina and other tissue may be excessive, thereby making it difficult to use the animal as an animal model of AMD. Therefore, in the present invention, the dosage of sodium iodate per vitreous body is preferably 0.5 mg to 2.5 mg and more preferably 1.0 mg to 1.5 mg. In addition, administration of sodium iodate into a vitreous body may be performed in a single administration or may be performed by dividing among multiple administrations given at suitable intervals.

There are no particular limitations on the method used to administer sodium iodate into a vitreous body. For example, a sodium iodate solution, obtained by dissolving sodium iodate in a suitable solvent, can be injected directly into a vitreous body. In the present invention, the solvent used to dissolve the sodium iodate is preferably water, phosphate-buffered saline (PBS) or a suitable buffer, and more preferably water or phosphate-buffered saline, from the viewpoint of reducing the effect of the solvent per se on the vitreous body.

In the method for producing an animal model of AMD according to the present invention, the animal in which AMD-like retinal degeneration is induced is only required to be a primate other than a human and may be a prosimian or simian. Examples of prosimians include lemurs, lorises, galagos and tarsiers, while examples of simians include spider monkeys, capuchin monkeys, marmosets, old world monkeys, colobines and anthropoids. In the method for producing an animal model of AMD according to the present invention, the non-human primate used to produce the AMD animal model is preferably a simian, more preferably an old world monkey, colobine or anthropoid, even more preferably a cynomolgus monkey, rhesus monkey, Japanese macaque, white gibbon, gorilla, orangutan, chimpanzee or bonobo, and still more preferably a cynomolgus monkey or rhesus monkey since the mechanism of the onset of AMD and the reaction to drugs are more similar to those of humans.

Thinning of the ONL, degeneration of RPE and geographic atrophy of the ocular fundus can be induced by administering sodium iodate into a vitreous body. Animals before and after administration of sodium iodate can be housed by providing feed similar to feed given when housing under ordinary conditions.

In human AMD and in human atrophic AMD in particular, one or more types of findings selected from the group consisting of thinning of the ONL and degeneration of RPE are observed in the retina. One or more types of findings selected from the group consisting of thinning of the ONL and degeneration of RPE are also be observed in the retina of a non-human primate model of AMD produced according to the method for producing an animal model of AMD according to the present invention.

Geographic atrophy is observed in the ocular fundus inhuman AMD, and particularly in human atrophic AMD. Geographic atrophy of the ocular fundus is also observed in a non-human primate model of AMD produced according to the method for producing an animal model of AMD according to the present invention. Geographic atrophy can be assessed using the same guidelines as those of human atrophic AMD (see, for example, Takahashi, K. et al., "Guidelines—Diagnostic Criteria for Atrophic Age-Related Macular Degeneration", Japanese Journal of Ophthalmology, Oct. 10, 2015, Vol. 19, No. 10, p. 671-677). More specifically, geographic atrophy refers to atrophy occurring in an area having a diameter of 6000 µm centering on the central fossa of the ocular fundus. Geographic atrophy typically exhibits a circular, oval, tufted or map-like shape, has a well-defined border, and has a diameter of 250 µm or more (roughly twice the diameter of the retinal vein at the edge of optic disk). In addition, since hypopigmentation or depigmentation changes are also observed in retinal pigment epithelium, large vessels in the choroid membrane can be clearly visualized, distinct hypofluorescence is exhibited in fundus autofluorescence findings, and hyperfluorescence is exhibited in fluorescein angiographic findings.

The resulting animal model of AMD is useful for analyzing the pathology of AMD, evaluating the efficacy of a test substance in the prevention or treatment of AMD, or screening substances effective in the prevention or treatment of AMD. Since this animal model of AMD exhibits pathology observed in human atrophic AMD, it is particularly useful for analyzing the pathology of atrophic AMD, evaluating the efficacy of a test substance in the prevention or treatment of atrophic AMD, or screening substances effective in the prevention or treatment of atrophic AMD.

More specifically, the therapeutic efficacy of a test substance against AMD is evaluated by administering the test compound that is a candidate compound of an AMD therapeutic agent to an animal model of AMD produced according to the method for producing an animal model of AMD according to the present invention followed by investigating the effect of the test compound on the eye, and particularly the effect thereof on histological characteristics of the retina unique to AMD. The test compound is evaluated as having a therapeutic effect on AMD in the case one or more characteristics of AMD selected from the group consisting of thinning of the ONL of the retina, degeneration of RPE and geographic atrophy of the ocular fundus demonstrates improvement as a result of administering the test substance in comparison with prior to ingestion of the test substance. There are no particular limitations on the method used to administer the test substance to the AMD animal model, and may be administered by oral administration, enema administration, intravenous administration or transnasal administration, or by injecting directly into the vitreous body or other tissue of the eye.

Test substances can also be screened for efficacy in preventing or treating AMD by similarly evaluating a plurality of test substances as to whether or not they are effective in treating or preventing AMD, and selecting a test substance evaluated as having a therapeutic or preventive effect as a substance that demonstrates efficacy in the prevention or treatment of AMD.

EXAMPLES

Although the following provides a more detailed explanation of the present invention by indicating examples thereof, the present invention is not limited to the following examples.

Furthermore, animal experiments carried out in the following examples and housing and management of animals used therein were carried out in strict compliance with the "Act on Welfare and Management of Animals" (Act No. 105, 1973), "Standards Relating to the Care and Management of Laboratory Animals and Relief of Pain" (Notification No. 88 of the Ministry of the Environment, 2006), "Basic policies for the conduct of animal experiments in research institutions under the jurisdiction of the Ministry of Health, Labor and Welfare (Notification of the Ministry of Health, Labor and Welfare, 2006) and "Guidelines for Proper Conduct of Animal Experiments" (Science Council of Japan, 2006) of Japan.

Example 1

A cynomolgus monkey model of AMD was produced to investigate whether or not the model exhibits histological characteristics unique to human AMD in the retina.

<Production of Animal Model Intravitreally Administered Sodium Iodate using a Cynomolgus Monkey>

50 µl of sodium iodate solution having a concentration of 20 mg/mL or 30 mg/mL was administered into the vitreous body of one eye of a cynomolgus monkey (dosage of 1 mg or 1.5 mg of sodium iodate per vitreous body) under ketamine anesthesia. Furthermore, the sodium iodate solution was prepared by dissolving sodium iodate in water for injection and preliminarily sterilizing by passing through a filter having a pore size of 0.22 µm.

Figure 2:
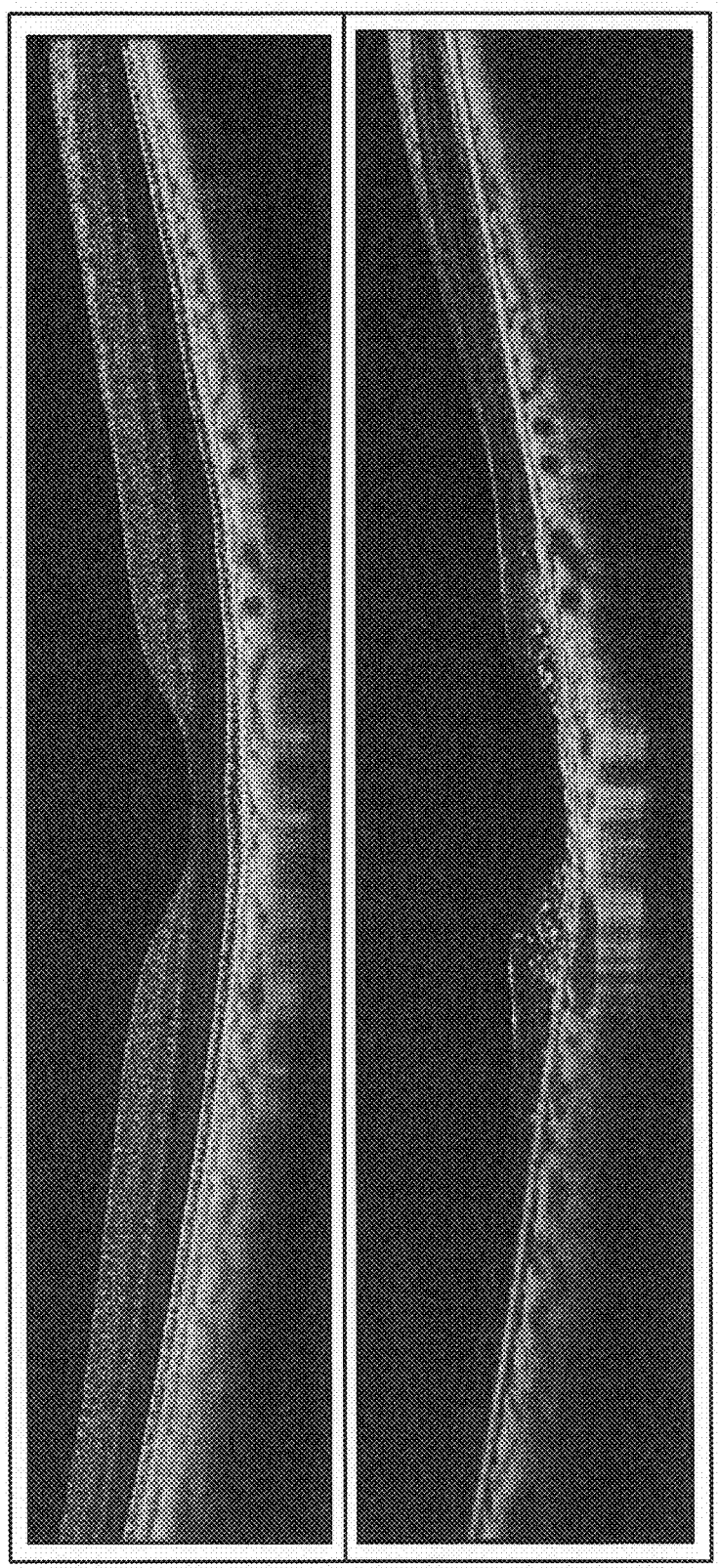
FIG. 2 depicts OCT images of the retina of an animal model intravitreally administered sodium iodate prior to administration of a sodium iodate solution (administration day 0) and on day 66 after administration in an Example 1.

Retinal thickness of the resulting animal model intravitreally administered sodium iodate was measured prior to administration of the sodium iodate solution (day 0 of administration) and on days 10 and 26 after administration. OCT images of the retina in the vicinity of the central fossa of the macula obtained from these measurements are shown in FIG. 1. The upper row of images represents membrane thickness of the retina as differences in contrast while the lower row indicates cross-sectional views of the retina. Measurement of membrane thickness of the retina was carried out by tracing the area on the OCT images corresponding to the outer layer of the retina followed by measuring thickness. OCT images of the retina on day 66 after administration of the sodium iodate solution following additional housing of the animal model are shown in FIG. 2. In FIG. 2, the upper image indicates a cross-sectional view of the retina prior to administration of the sodium iodate solution while the lower image indicates a cross-sectional view of the retina on day 66 after administration of the sodium iodate solution.

In FIGS. 1 and 2, the area where the membrane thickness of the central portion has become thin is the central fossa of the macula. As shown in FIG. 1, retinal thickness became thin centering on the central fossa of the macula on day 10 after administration of the sodium iodate solution, and this thin area expanded further on day 26 after administration of the sodium iodate solution. This reduction in membrane thickness in the central fossa of the macula and the vicinity thereof mainly indicates thinning of the ONL. Moreover, based on the cross-sectional views of the retina shown in FIG. 2, in addition to thinning of the ONL, RPE and the photoreceptor cell layer (ellipsoid zone and interdigitation zone) were no longer visible in the central fossa, and disruption of the external limiting membrane and enhancement of choroidal signal were also observed on day 66 after administration. On the basis of these results, administration of sodium iodate into a vitreous body was determined to induce thinning of the ONL and degeneration of RPE around the central fossa of the macula, and the non-human primate model intravitreally administered sodium iodate was determined to exhibit clinical findings typically observed in human atrophic AMD.

Example 2

A cynomolgus monkey model of AMD was produced to investigate whether or not the model exhibits histological characteristics unique to human AMD in the ocular fundus and central fossa of the macula.

<Funduscopy, Fundus Autofluorescence and Fluorescein Angiography>

More specifically, 1.5 mg of sodium iodate per vitreous body were administered into the right eye of a 9-year-old cynomolgus monkey in the same manner as Example 1 to produce an animal model of intravitreal administration of sodium iodate followed by investigating the ocular fundus by funduscopy and fundus autofluorescence prior to administration of the sodium iodate solution (day 0 of administration) and on days 38 and 66 after administration. Funduscopy and fundus autofluorescence were carried out in accordance with routine methods using a fundus camera equipped with an autofluorescence imaging function. In addition, the animal model also underwent fluorescein angiography on day 66 after administration. Fluorescein angiography was carried out in accordance with routine methods using a fundus camera capable of observing fluorescent light after having intravenously injected the animal model with fluorescein.

Figure 3:
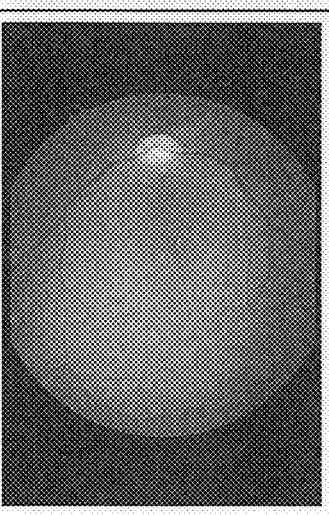
FIG. 3 depicts fundus findings (upper row) and fundus autofluorescence findings (lower row) in an animal model intravitreally administered sodium iodate prior to administration of a sodium iodate solution (day 0 of administration), on day 38 after administration and on day 66 after administration in an Example 2.

The results of funduscopy and fundus autofluorescence are shown in FIG. 3. The upper row of images depicts fundus findings, while the lower row of images depicts fundus autofluorescence findings. Although atrophy was not observed prior to administration (indicated by "Day 0" in the figure), an atrophic lesion having a diameter equal to roughly 2 times to 2.5 times the diameter of the optic disk (diameter of the retinal vein on the edge of the optic disk) was observed centering on the central fossa of the macula on day 38 after administration (indicated by "Day 38" in the figure) and on day 66 after administration (indicated by "Day 66" in the figure). In addition, this atrophic lesion demonstrated prominent hypofluorescence in fundus autofluorescence findings. Since this atrophic lesion exhibited a well-defined border and distinct hypofluorescence in fundus autofluorescence findings in addition to geographic atrophy and the increased diameter thereof, the animal model was judged to exhibit geographic atrophy. This geographic atrophy was classified clinically as central geographic atrophy since the atrophy had extended to the central fossa.

Figure 4:
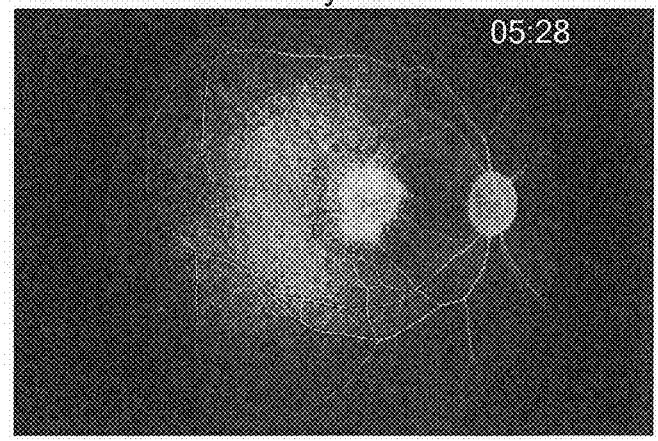
FIG. 4 depicts fluorescein angiographic findings in an animal model intravitreally administered sodium iodate on day 66 after administration of a sodium iodate solution in an Example 2.

Fluorescein angiography findings are shown in FIG. 4. As a result, the area with the atrophic lesion demonstrated prominent hyperfluorescence due to a window defect (state that causes an abnormality of RPE in which fluorescence passes through the choroid membrane) in the same manner as human atrophic AMD. In addition, drusen-like sites of hyperfluorescence were sporadically located around the area of the atrophic lesion. This area of the atrophic lesion was able to be identified as geographic atrophy on the basis of these findings as well.

<HE Staining of Tissue at Sites Surrounding the Central Fossa>

Tissue at sites surrounding the central fossa in the animal model intravitreally administered sodium iodate on day 66 after administration of sodium iodate solution was stained with hematoxylin-eosin (HE) stain to investigate the morphology of the RPE layer. After sacrificing the animal, the tissue was fixed with 2.5% glutaraldehyde followed by HE staining in accordance with routine methods.

Figure 5:
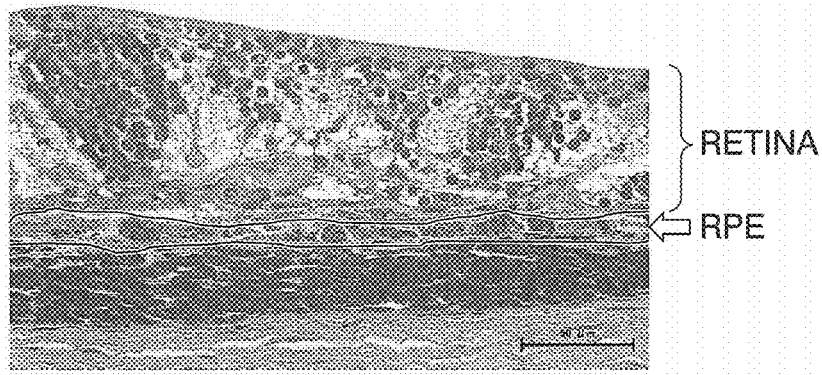
FIG. 5 depicts the results of HE staining of tissue at the site of the central fossa in an animal model intravitreally administered sodium iodate on day 66 after administration of the sodium iodate solution in an Example 2.

Images of the HE-stained tissue at sites surrounding the central fossa are shown in FIG. 5. Degeneration and loss of the RPE layer (framed in black in the figure) were able to be confirmed. In addition, degeneration occurred throughout the entire retina and photoreceptor cells were no longer visible.

On the basis of these findings, the animal model intravitreally administered sodium iodate produced in this example was confirmed to exhibit characteristic findings of human atrophic AMD in the form of geographic atrophy, RPE degeneration and damage to photoreceptor cells, and was therefore confirmed to be preferable as an animal model of human atrophic AMD.

Reference Example 1

A cynomolgus monkey model of light-induced retinopathy was produced to investigate the morphology of the retinal tissue of that model by HE staining.

<Production of Cynomolgus Monkey Model of Light-Induced Retinopathy>

One eye of a cynomolgus monkey immobilized while facing upward was illuminated for 30 minutes with blue light at an illumination intensity of 1800 lux and wavelength of 460 nm from directly overhead at a distance of 5 cm from the eye using a variable wavelength light source. This procedure was carried out for 3 days to produce an animal model of light-induced retinopathy.

<HE Staining of Tissue Surrounding Central Fossa>

Tissue at sites surrounding the central fossa of the resulting animal model of light-induced retinopathy was subjected to HE staining to investigate the morphology of the RPE layer. HE staining was carried out in the same manner as Example 2.

Figure 6:
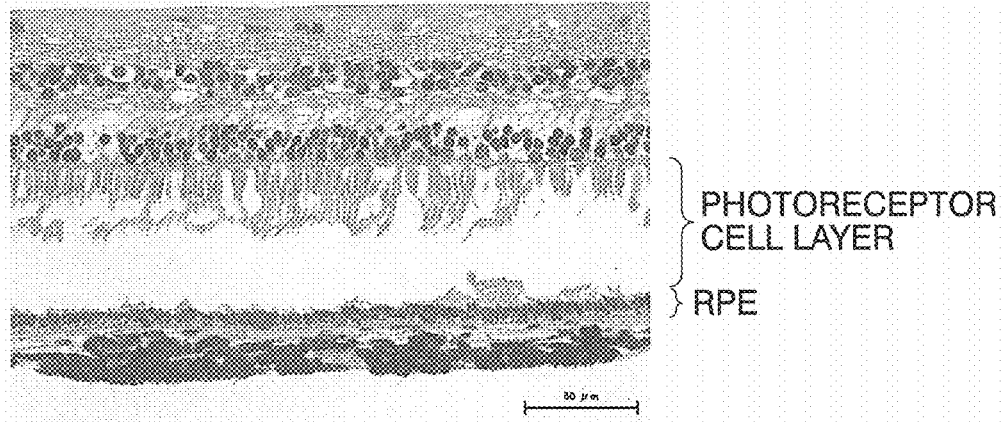
FIG. 6 depicts the results of HE staining of tissue at the site of the central fossa in an animal model of light-induced retinopathy in a Reference Example 1.

Images of the HE-stained tissue at sites surrounding the central fossa are shown in FIG. 6. Significant degeneration of the RPE layer was not observed. Detachment of the photoreceptor cell layer from the RPE layer was an artifact that occurred during specimen preparation. In the figure, the long narrow cells in the photoreceptor cell layer are photoreceptor cells. In other words, although this animal model of light-induced retinopathy exhibited damage to the retina, the pathology thereof differed from findings observed in human atrophic AMD, and was therefore determined to be unlikely to serve as a suitable animal model of human atrophic AMD.

The invention claimed is:

1. A method for producing an animal model of age-related macular degeneration (AMD), comprising the steps of: administering sodium iodate into a vitreous body of a non-human primate; and observing development of thinning of an outer nuclear layer (OLN) and degeneration of a retinal pigment epithelium (RPE) of a retina in the periphery of a central fossa of a macula in said vitreous body of said non-human primate, thereby producing an animal model of AMD.

2. The method for producing an animal model of age-related macular degeneration according to claim 1, wherein a sodium iodate solution, obtained by dissolving sodium iodate in water or phosphate-buffered saline, is administered into a vitreous body.

3. The method for producing an animal model of age-related macular degeneration according to claim 1, wherein the animal is a cynomolgus monkey or rhesus monkey.

4. The method for producing an animal model of age-related macular degeneration according to claim 1, wherein geographic atrophy occurs in the ocular fundus of the resulting animal model of age-related macular degeneration.

5. A method of screening substances effective in the treatment of AMD, comprising the steps of: producing a non-human primate model of AMD according to the method for producing an animal model of AMD according to claim 1, and evaluating the efficacy of a test substance in the treatment of the non-human primate model of AMD.

6. A method of screening substances effective in the treatment of AMD, comprising the steps of: producing a non-human primate model of AMD according to the method for producing an animal model of AMD according to claim 1, evaluating the efficacy of a test substance in the treatment of the non-human primate model of AMD, and selecting the test substance as a substance effective in treatment of AMD if one or more conditions have been met, wherein the one or more conditions are selected from the group consisting of: reduced thinning of the ONL and reduced degeneration of the RPE of the retina following treatment with the test substance as compared to before treatment with the test substance.

7. The method for producing an animal model of AMD according to claim 1, wherein the sodium iodate is administered in a dosage of 0.5 mg to 2.5 mg per vitreous body.

* * * * *